(12) United States Patent
Yanagihara

(10) Patent No.: US 8,933,241 B2
(45) Date of Patent: *Jan. 13, 2015

(54) METHOD FOR PRODUCING OLMESARTAN MEDOXOMIL

(75) Inventor: Shigeo Yanagihara, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/266,885

(22) PCT Filed: Apr. 27, 2010

(86) PCT No.: PCT/JP2010/057403
§ 371 (c)(1),
(2), (4) Date: Nov. 17, 2011

(87) PCT Pub. No.: WO2010/126013
PCT Pub. Date: Nov. 4, 2010

(65) Prior Publication Data
US 2012/0071665 A1  Mar. 22, 2012

(30) Foreign Application Priority Data
Apr. 28, 2009  (JP) ................. 2009-109159

(51) Int. Cl.
C07D 405/14 (2006.01)
A61K 31/4178 (2006.01)

(52) U.S. Cl.
CPC .......... A61K 31/4178 (2013.01); C07D 405/14 (2013.01)
USPC ....................................... 548/253

(58) Field of Classification Search
USPC .......................... 514/382; 548/250, 252, 253
See application file for complete search history.

(56) References Cited

U.S. PATENT DOCUMENTS

| | | | |
|---|---|---|---|
| 5,616,599 A | 4/1997 | Yanagisawa et al. | |
| 5,646,171 A | 7/1997 | Yanagisawa et al. | |
| 5,744,612 A | 4/1998 | Koguro | |
| 6,040,454 A | 3/2000 | Koguro | |
| 7,528,258 B2* | 5/2009 | Hedvati et al. | 548/253 |
| 7,563,814 B2* | 7/2009 | Hedvati et al. | 514/385 |
| 8,048,904 B2* | 11/2011 | Ramanjaneyulu et al. | 514/382 |
| 8,076,492 B2 | 12/2011 | Pathi et al. | |
| 2006/0069141 A1 | 3/2006 | Hedvati et al. | |
| 2006/0074117 A1* | 4/2006 | Hedvati et al. | 514/381 |
| 2006/0149078 A1 | 7/2006 | Hedvati et al. | |
| 2007/0054948 A1 | 3/2007 | Hedvati et al. | |
| 2008/0076932 A1 | 3/2008 | Razzetti et al. | |
| 2009/0281327 A1 | 11/2009 | Ramanjaneyulu et al. | |
| 2010/0076200 A1 | 3/2010 | Hedvati et al. | |
| 2011/0092713 A1 | 4/2011 | Sato | |

FOREIGN PATENT DOCUMENTS

| | | |
|---|---|---|
| CN | 1976926 A | 6/2007 |
| CN | 1993355 A | 7/2007 |
| CN | 101094850 A | 12/2007 |
| CN | 101238119 A | 8/2008 |
| EP | 0796852 A1 | 9/1997 |
| EP | 0503785 B1 | 4/2001 |
| EP | 2036904 A1 | 3/2009 |
| JP | 7-121918 | 12/1995 |
| JP | 3521304 B2 | 4/2004 |
| JP | 3671266 B2 | 4/2004 |
| JP | 2004-217542 A | 8/2004 |
| JP | 2006-111586 A | 4/2006 |
| JP | 2007-509992 | 4/2007 |
| JP | 2007-509993 | 4/2007 |
| JP | 2007-526342 | 9/2007 |
| JP | 2008-088172 | 4/2008 |
| WO | 2004065383 | 8/2004 |
| WO | WO 2006/029056 | 3/2006 |
| WO | WO 2006/029057 | 3/2006 |
| WO | WO 2006/073519 | 7/2006 |
| WO | 2007017135 A2 | 2/2007 |
| WO | WO 2007/047838 | 4/2007 |
| WO | WO 2007/048361 | 5/2007 |
| WO | WO 2007/148344 | 12/2007 |
| WO | WO 2008/043996 | 4/2008 |
| WO | WO 2009/019304 | 2/2009 |
| WO | WO 2010/026255 | 3/2010 |
| WO | WO 2011/014611 | 2/2011 |
| WO | WO 2012/001694 | 1/2012 |

OTHER PUBLICATIONS

Yanagisawa, H, "Nonpeptide Angiotensin II Receptor Antagonists: Synthesis, Biological Activities, and Structure-Activity Relationships of Imidazole-5-carboxylic Acids Bearing Alkyl, Alkenyl, and Hydroxyalkyl Substituents at the 4-Position and Their Related Compounds", J. Med. Chem., 39, 323-338 (1996).

Koike, H., "Olmesartan Medoxomil, a Novel Potent Angiotensin II Blocker", Annu. Rep. Sankyo Res. Lab. (Sankyo Kenkyusho Nempo) 55, 1-91 (2003).

International Preliminary Report on Patentability, issued in PCT/JP2010/057403, mailed Nov. 9, 2011.

International Search Report, issued in PCT/JP2010/057403, mailed Jun. 8, 2010.

Written Opinion of the International Searching Authority, issued in PCT/JP2010/057403, mailed Jun. 8, 2010.

International Preliminary Report on Patentability, issued in PCT/JP2010/057404, mailed Nov. 9, 2011.

International Search Report, issued in PCT/JP2010/057404, mailed Jun. 8, 2010.

Written Opinion of the International Searching Authority, issued in PCT/JP2010/057404, mailed Jun. 8, 2010.

U.S. Appl. No. 13/266,967, filed Nov. 8, 2011, Hiroshi Kiyota.

Supplementary European Search Report, issued in EP Application No. 10769711.2, mailed Sep. 6, 2012.

(Continued)

Primary Examiner — Joseph Kosack
(74) Attorney, Agent, or Firm — Locke Lord, LLP

(57) ABSTRACT

A method for producing high-purity olmesartan medoxomil is provided in which a solvent containing water is used in steps of tritylation and DMDO esterification of olmesartan.

16 Claims, No Drawings

(56) References Cited

OTHER PUBLICATIONS

Supplementary European Search Report, issued in EP Application No. 10769712.0, mailed Aug. 24, 2012.
English Translation of Opposition filed by Tecnoquimicas S.A., against Colombia App. No. 11-161167, Gazette 647, Publication No. 817, Jun. 29, 2012.
English Translation of Defense of Opposition by Tecnoquimicas S.A., against Colombia App. No. 11-161167, Gazette 647, Publication No. 817, Jun. 29, 2012.
English Translation of Opposition filed by Laboratorio Franco Colombiano S.A.S. Lafrancol S.A.S., against Colombia App. No. 11-161167, Gazette 647, Publication No. 817, Jun. 29, 2012.
Giron, D., Technochimica acta 248-1-59, Elsevier Science B.V., 1995, pp. 3 to 11.
J. Garrido, Form and Structure of Crystals, (op. cit.), chapter V, pp. 204, 212 (with English translation).
A.R. Verna, P. Krishna—"Polytypism in crystals", John Wiley and Son Inc., New York 1966.
Vila Jato J.L. Technologia Farmaceutica, vol. 1, pp. 42 to 49 (cited in Colombia opposition; no copy available).
Doelke E. Crystalline modifications and polymorphism changes during drug manufacture, Ann Pharm Fr. May 2002; 60(3): 161-76 (with English abstract).
The Merck Index. "An encyclopedia of chemicals, drugs, and biological. Fourteenth Edition." 2006. p. 1178. (Olmesartan).
EPO Third Party Observation, filed Sep. 21, 2012 against EPA No. 10769712.0.
Vila Jato, J.L., Technologia Farmaceutica, vol. 1, pp. 42 to 49 (cited at pp. 3, 4 of English translation of Colombia opposition filed by Tecnoquimicas S.A., previously submitted).
Office Action and Search Report issued in Chinese Application No. 2010800189009; dated Jul. 31, 2013.
Office Action and Search Report issued in Chinese Application No. 2010800188970; dated Aug. 12, 2013.
Office Action issued in Colombian Application No. 11161167; dated Aug. 28, 2013.
International Preliminary Examination Report on Patentability for International Application No. PCT/JP2009/060419, corresponding to related U.S. Appl. No. 12/996,697, issued on Dec. 13, 2010 and the English translation issued on Jan. 11, 2011.
International Search Report for International Application No. PCT/JP2009/060419, corresponding to related U.S. Appl. No. 12/996,697, mailed on Aug. 11, 2009 (English & Japanese).
Written Opinion of the International Searching Authority for International Application No. PCT/JP2009/060419, corresponding to related U.S. Appl. No. 12/996,697, mailed on Aug. 11, 2009 (English & Japanese).
Marceau, P. et al. "Graphite intercalation compounds as precursors of activated metals. II *. Synthesis of beta, gamma-unsaturated ketones through condensation of allylic organozinc derivatives with nitriles." Journal of Organometallic Chemistry, 403:21-27 (1991).
Akiyama, Y. et al. "Reaction of organocadmium reagents with ethyl cyanoformate: preparation of alpha-keto esters." Chemistry Letters, 1231-1232 (1983).
Lee, A.S-Y., et al. "Synthesis of allyl ketone via Lewis acid promoted Barbier-type reaction." Tetrahedron Letters, 41:8803-8806 (2000).
EP Search Report for EP 09762446, corresponding to related U.S. Appl. No. 12/996,697, dated Aug. 29, 2011.
Khurana, J., et al. "A novel method of synthesis of 1,2-diketones from 1,2-diols using N-bromosuccinimide," Tetrahedron Letters, 44:4909-4912 (2003).
Grant, D.J.W., "Theory and Origin of Polymorphism", in HG Brittain (ed.) Polymorphism in Pharmaceutical Solids. Marcel Dekker, Inc., New York, Ch. 1, pp. 1-33, Jan. 1999.
Guillory, JK, "Generation of polymorphs, hydrates, solvates, and amorphous solids", in HG Brittain (ed.) Polymorphism in Pharmaceutical Solids. Marcel Dekker, Inc., New York, Ch. 5, pp. 183-226. Jan. 1999.
Caira, MR, "Crystalline Polymorphism of organic compound", Topics in Current Chemistry, Springer, Berlin, De., vol. 198, pp. 163-208, Jan. 1, 1998.
Byrn, S., "Pharmaceutical Solids: A Strategic Approach to Regulatory Considerations", Pharmaceutical Research, vol. 12(7), pp. 945-954, Jul. 1995.
Preparado Farmaceutoco Y Su Elaboracion, in Remington 2 Farmacia 17a edicion; Marino, M.A. (ed.); Editorial Medica Panamericana, S.A.; pp. 1912-1920 (Jul. 1987).
Preformulation, in Remington: The Science and Practice of Pharmacy, Nineteenth Edition, vol. II; Gennaro, A.R. (ed.); Mack Publishing Company, Easton, PA; pp. 1451-1457 (Jun. 1995).
Information Statement submitted by anonymous 3rd-party in the corresponding Japanese Application No. JP 2011-511396 of related U.S. Appl. No. 13/266,967, reported from the JPO to the assignee on Jun. 4, 2014.
English translation of Information Statement submitted by anonymous 3rd-party in corresponding Japanese Application No. JP 2011-511396 of related U.S. Appl. No. 13/266,967, reported from the JPO to the assignee on Jun. 4, 2014.
Statement of Case on Behalf of the Opponent, filed in corresponding Israeli Patent Application No. 215966, mailed on Sep. 27, 2014 (Hebrew and English Translation).
Li, et al., "Synthetic approaches to the 2002 new drugs", Mini-Reviews in Medicinal Chemistry, 4:207-233, (2004).
Bettelheim, et al., "Introduction to general, organic, and biochemistry, 8th Ed.", pp. 380-381 (2007).

* cited by examiner

METHOD FOR PRODUCING OLMESARTAN MEDOXOMIL

This application is a national phase entry under 35 U.S.C. §371 of International Application Number PCT/JP2010/057403, filed on Apr. 27, 2010, entitled "METHOD FOR PRODUCING OLMESARTAN MEDOXOMIL", which claims the benefit of Japanese Patent Application Number JP 2009-109159, filed on Apr. 28, 2009, all of which are hereby incorporated by reference.

FIELD OF THE INVENTION

The present invention relates to a method for producing high-purity olmesartan medoxomil.

BACKGROUND

Olmesartan medoxomil, which is an angiotensin II receptor antagonist, is useful as an active ingredient in medicaments for treatment and prophylaxis of hypertension (for example, Patent documents 1 to 5 or Non-patent documents 1 and 2). Techniques for producing high-purity olmesartan medoxomil are necessary for use of olmesartan medoxomil as a medicament.

Olmesartan medoxomil is produced from olmesartan by the steps described below, but there is the problem that olmesartan which is a starting material, olmesartan medoxomil dehydrate which is a by-product, or the like, is present as an impurity.

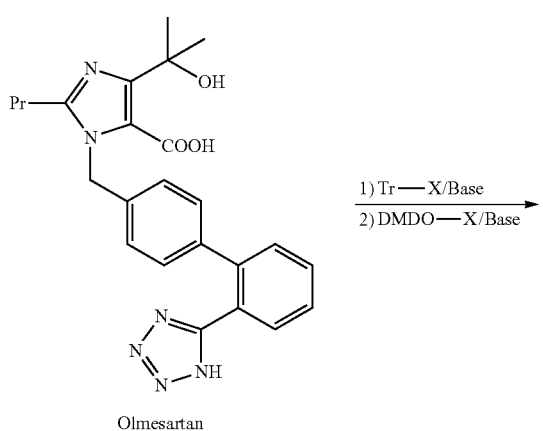

Olmesartan

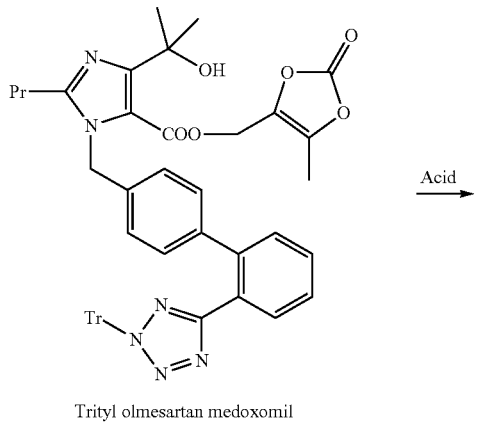

Trityl olmesartan medoxomil

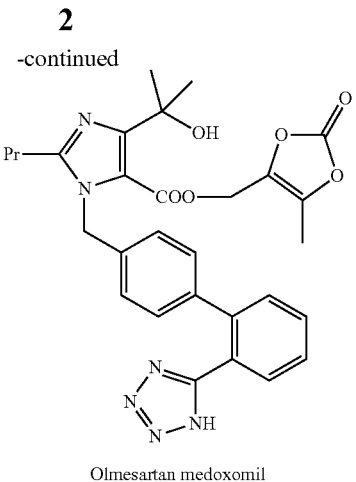

Olmesartan medoxomil

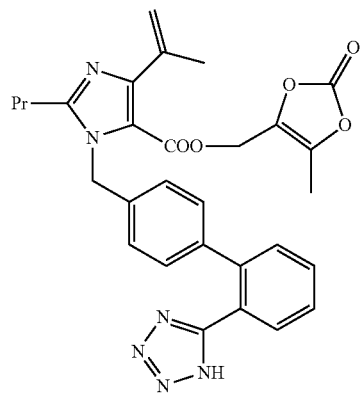

Olmesartan medoxomil dehydrate

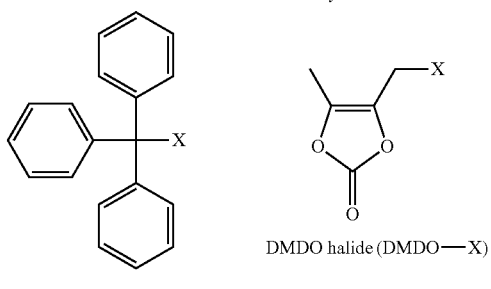

Trityl halide (Tr—X)     DMDO halide (DMDO—X)

PRIOR ART DOCUMENTS

Patent Documents

Patent document 1: Japanese Examined Patent Application (Kokoku) No. Hei 7-121918 (Japanese Patent No. 2082519)
Patent document 2: U.S. Pat. No. 5,616,599
Patent document 3: International Patent Publication No. WO2006/029056
Patent document 4: International Patent Publication No. WO2006/029057
Patent document 5: International Patent Publication No. WO2006/073519

Non-Patent Documents

Non-patent document 1: J. Med. Chem., 39, 323-338 (1996)
Non-patent document 2: Annu. Rep. Sankyo Res. Lab. (Sankyo Kenkyusho Nempo) 55, 1-91 (2003)

SUMMARY OF THE INVENTION

Object of the Invention

It is an object of the present invention to provide a method for producing high-purity olmesartan medoxomil in which the contents of impurities such as olmesartan and olmesartan medoxomil dehydrate, especially the content of olmesartan medoxomil dehydrate, are reduced.

Means for Achieving the Object

The present inventors have conducted intensive research on methods for producing high-purity olmesartan medoxomil in which the contents of impurities such as olmesartan, olmesartan medoxomil dehydrate and olmesartan lactone are reduced, and as a result it was found, surprisingly, that it is possible to reduce the content of olmesartan medoxomil dehydrate by employing as a reaction solvent a solvent containing water, which was thought to lower reaction efficiency in the steps of tritylation and DMDO esterification, and the invention has been completed.

The invention provides a method for producing high-purity olmesartan medoxomil which comprises steps of tritylation and DMDO esterification using a solvent containing water.

The invention encompasses the following aspects (1) to (21).

(1) A method for producing olmesartan medoxomil comprising a step in which trityl olmesartan medoxomil is produced by (i) reacting olmesartan with trityl halide and then (ii) reacting it with DMDO halide, in a solvent in the presence of a base, wherein water is present in the reaction mixture in the tritylation step (i) and the DMDO esterification step (ii).

(2) The production method according to (1), wherein olmesartan medoxomil is produced by removing the trityl group from trityl olmesartan medoxomil.

(3) The production method according to (1) or (2), wherein the water content in the reaction mixture is 0.3 (w/w) % or more.

(4) The production method according to (1) or (2), wherein the water content in the reaction mixture is from 0.3 to 3.0 (w/w) %.

(5) The production method according to (1) or (2), wherein the water content in the reaction mixture is from 0.3 to 1.5 (w/w) %.

(6) The production method according to (1) or (2), wherein the water content in the reaction mixture is from 0.4 to 1.3 (w/w) %.

(7) The production method according to (1) or (2), wherein 1.0 to 28 (w/w) % water to olmesartan is added to the reaction mixture.

(8) The production method according to (1) or (2), wherein 1.0 to 13 (w/w) % water to olmesartan is added to the reaction mixture.

(9) The production method according to (1) or (2), wherein 2.0 to 10 (w/w) % water to olmesartan is added to the reaction mixture.

(10) The production method according to any one of (1) to (9), wherein the reaction solvent is used in a 5 to 20 (v/w)-fold amount to olmesartan.

(11) The production method according to any one of (1) to (10), wherein the reaction solvent is acetone.

(12) The production method according to any one of (1) to (11), wherein the base is 1,8-diazabicyclo[5,4,0]-7-undecene.

(13) The production method according to any one of (1) to (12), wherein the halide portion of the trityl halide and the DMDO halide is chloride.

(14) Olmesartan medoxomil obtained by the method according to any one of (1) to (13), which comprises 0.3% or less of olmesartan medoxomil dehydrate.

(15) Olmesartan medoxomil obtained by the method according to any one of (1) to (13), which comprises 0.25% or less of olmesartan medoxomil dehydrate.

(16) Olmesartan medoxomil obtained by the method according to any one of (1) to (13), which comprises 0.2% or less of olmesartan medoxomil dehydrate.

(17) Olmesartan medoxomil comprising 0.3% or less of olmesartan medoxomil dehydrate.

(18) Olmesartan medoxomil comprising 0.25% or less of olmesartan medoxomil dehydrate.

(19) Olmesartan medoxomil comprising 0.2% or less of olmesartan medoxomil dehydrate.

(20) A medicament comprising olmesartan medoxomil according to any one of (14) to (19) as an active ingredient.

(21) A medicament for treatment or prophylaxis of hypertension comprising olmesartan medoxomil according to any one of (14) to (19) as an active ingredient.

In the present invention, olmesartan, trityl olmesartan medoxomil, olmesartan medoxomil, olmesartan medoxomil dehydrate, trityl halide and DMDO halide are compounds represented by the structural formulas described in the figure above, respectively. In the structural formulas of trityl halide and DMDO halide, each X independently represents a halogen atom such as chloro, bromo or iodo. Tr represents triphenylmethyl. DMDO represents the portion in which X is eliminated in the structural formula of DMDO halide. Trityl olmesartan and trityl olmesartan medoxomil dehydrate represent compounds represented by the structural formulas described in the figure below, respectively.

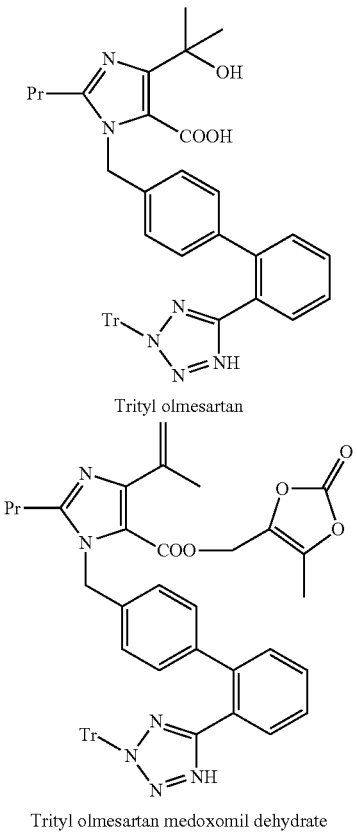

Trityl olmesartan

Trityl olmesartan medoxomil dehydrate

The compound names of olmesartan, trityl olmesartan medoxomil, olmesartan medoxomil, olmesartan medoxomil dehydrate and DMDO chloride (DMDO-Cl) are indicated in Examples described below.

EFFECT OF THE INVENTION

In the present invention, it is possible to provide high-purity olmesartan medoxomil in which the contents of impurities such as olmesartan and olmesartan medoxomil dehydrate, especially the content of olmesartan medoxomil dehydrate, are reduced.

DETAILED DESCRIPTION

Olmesartan as the starting material used in the production method of the present invention can be easily produced according to the method described in Japanese Examined Patent Application (Kokoku) No. Hei 7-121918 (Japanese Patent No. 2082519; U.S. Pat. No. 5,616,599) or the like.

The method for producing high-purity olmesartan medoxomil by carrying out the present invention is as follows.

(Tritylation Step)

This step is a step in which trityl olmesartan is produced by reacting olmesartan with a trityl halide in a solvent in the presence of a base.

Trityl chloride or trityl bromide is usually used as the trityl halide, and trityl chloride is preferable.

The solvent used is not particularly restricted, and solvents which are easily miscible with water, including ketones such as acetone and methyl ethyl ketone, ethers such as diethyl ether and tetrahydrofuran and esters such as methyl acetate and ethyl acetate, are preferable. Among them, ketones are preferable and acetone is most preferable.

The reaction solvent is usually used in a 5 to 20 (v/w)-fold amount to olmesartan, and this is not particularly restrictive.

The base used is not particularly restricted, and an amine such as triethylamine, diisopropylethylamine, pyridine or 1,8-diazabicyclo[5,4,0]-7-undecene (DBU) is preferably used, and DBU is most preferable.

The reaction temperature is not particularly restricted, and the reaction is usually carried out at a temperature in the range of 0° C. to the boiling point of the solvent, and preferably at 20 to 60° C.

Upon completion of the reaction, trityl olmesartan may be isolated by a method usually used in the field of synthetic organic chemistry. The reaction mixture may also be used directly in the subsequent DMDO esterification step, without isolation.

(DMDO Esterification Step)

This step is a step in which trityl olmesartan medoxomil is produced by reacting trityl olmesartan with a DMDO halide in a solvent in the presence of a base.

DMDO chloride or DMDO bromide is usually used as the DMDO halide, and DMDO chloride is preferable.

The solvent used is the same as in the tritylation step above, and ketones, especially acetone, are preferable.

The base used is the same as in the tritylation step above, and DBU is preferable.

The reaction temperature is not particularly restricted, and the reaction is usually carried out at a temperature in the range of 0° C. to the boiling point of the solvent, and preferably at 20 to 60° C.

Upon completion of the reaction, trityl olmesartan medoxomil may be isolated by a method usually used in the field of synthetic organic chemistry.

When the tritylation step and the DMDO esterification step are conducted in acetone containing water, trityl olmesartan medoxomil may be obtained as crude crystals by adding 20 to 40% volume of water to the reaction mixture and cooling the reaction mixture. Purified crystals of trityl olmesartan medoxomil may be obtained by dissolving crude crystals of it in a solvent, treating with an adsorbent, and adding water after removal of the adsorbent to be crystallized. Specifically, the purified crystals may be obtained by treating the crude crystals with active carbon in acetone, and adding water after removal of the active carbon.

The present invention is characterized in that water is present in the reaction mixture in the tritylation step and the DMDO esterification step described above.

The amount of water present in the reaction mixture can be usually adjusted by adding water to the reaction mixture. Water may be added at once in the tritylation step, and may also be added separately in the tritylation step and in the DMDO esterification step.

The amount of water added to the reaction mixture is preferably adjusted in consideration of the water content in the starting materials, reaction reagents and solvent, so as to make the amount of water present in the reaction mixture as a whole (the water content in the reaction mixture) appropriate.

The water content in the reaction mixture is defined as the proportion (w/w) % of the total water content (weight) to the total weight of the whole reaction mixture, by totaling the water contents in the starting materials, reaction reagents and reaction solvent.

The water contents in the starting materials, reaction reagents and reaction solvent may be measured using a Karl Fischer moisture measuring apparatus. For commercially available reagents or solvents, these may be calculated using the measured values or standard values described in the manufacturer's package insert.

The lower limit of the water content in the reaction mixture is usually 0.3 (w/w) % or more, and preferably 0.4 (w/w) % or more and most preferably 0.5 (w/w) % or more.

The upper limit of it is usually 3 (w/w) % or less, and preferably 2 (w/w) % or less and most preferably 1.5 (w/w) % or less.

When the water content in the reaction mixture increases, the efficiency of the tritylation and DMDO esterification reactions is reduced, potentially lengthening the reaction time or lowering the reaction yield. Therefore, in consideration of both impurity content reduction and reaction efficiency, the water content in the reaction mixture is preferably 1.3 (w/w) % or less.

The water content in the reaction mixture is usually from 0.3 to 3.0 (w/w) %, preferably from 0.3 to 1.5 (w/w) %, more preferably from 0.4 to 1.5 (w/w) % and most preferably from 0.4 to 1.3 (w/w) %.

The amount of water added to the reaction mixture can be more conveniently adjusted in terms of the proportion (w/w) % to olmesartan (weight) as the starting material.

Olmesartan as the starting material having a water content of from 0.3 to 0.5 (w/w) % is usually used. DBU having a water content of about 0.5% is usually used. Triphenylmethyl chloride (TPC) and DMDO chloride usually contain essentially no water. When acetone is used as a solvent, that having a water content of about 0.2% is usually used. Acetone in a 5 to 20 (v/w)-fold amount to olmesartan is usually used.

When the reaction is carried out under these conditions, the lower limit of the amount of added water is usually 1.0 (w/w) % or more, preferably 2.0 (w/w) % or more and most preferably 4.0 (w/w) % or more, to olmesartan. When the water content in the starting materials, reagents and solvent is more than described above, the amount of water added to the reaction mixture may be less.

The upper limit of it is usually 28 (w/w) % or less, and preferably 18 (w/w) % or less and most preferably 13 (w/w) % or less. In consideration of both impurity content reduction and reaction efficiency, it is preferably 10 (w/w) % or less.

The amount of water added to the reaction mixture is usually from 1.0 to 28 (w/w) %, preferably from 1.0 to 13 (w/w) %, more preferably from 2.0 to 13 (w/w) % and most preferably from 2.0 to 10 (w/w) %, to olmesartan.

The trityl olmesartan medoxomil obtained in the steps described above may be converted to high-purity olmesartan medoxomil by a detritylation step (a step of removing a trityl group). The method for producing olmesartan medoxomil in the present invention comprises a step in which olmesartan medoxomil is produced by applying trityl olmesartan medoxomil obtained in the steps described above to a detritylation step. It is a feature of the present invention that the content of olmesartan medoxomil dehydrate is reduced. The detritylation step may be by methods described in, for example, Patent document 1, Patent document 2, Non-patent document 1 or Non-patent document 2, and it is not particularly restricted thereto.

Olmesartan medoxomil obtained by the production method of the present invention comprises 0.3% or less of olmesartan medoxomil dehydrate, preferably 0.25% or less and more preferably 0.2% or less. The content may be represented as the area percentage (%) measured by a liquid chromatography method, and for example, it may be determined by the method described in the section "Method of measuring contents of olmesartan medoxomil and impurity" below.

When high-purity olmesartan medoxomil obtained in the present invention is used as a medicament, the dosage may be varied based on various conditions including patient symptoms, age, body weight or the like. The dosage differs depending on the symptoms, age, etc., and in oral administration, it may be 0.001 mg/kg (preferably 0.01 mg/kg) as the lower limit and 10 mg/kg (preferably 1 mg/kg) as the upper limit per day, with 1 to 6 times of administration a day depending on the symptoms.

When used for an adult human, it is usually administered orally at 5 to 40 mg dosage once a day, and most preferably a tablet comprising a dosage selected from 5 mg, 10 mg, 20 mg and 40 mg is administered orally once a day.

A medicament comprising high-purity olmesartan medoxomil obtained in the present invention is effective for prophylaxis or treatment of hypertension or diseases derived from hypertension (more specifically, hypertension, cardiopathies [angina pectoris, myocardial infarction, arrhythmia, cardiac failure or cardiac hypertrophy], renal diseases [diabetic nephropathy, glomerular nephritis or renal sclerosis], cerebrovascular diseases [cerebral infarction or cerebral hemorrhage]) or the like.

EXAMPLES

The present invention is explained in more detail through the following Examples or the like, and the present invention is not limited thereto.

Example 1

(1) Tritylation and DMDO Esterification Reactions 4-(1-Hydroxy-1-methylethyl)-2-propyl-1-[[2'-[1H-tetrazol-5-yl]biphenyl-4-yl]methyl]imidazole-5-carboxylic acid [olmesartan] (20 g), acetone (155 ml), 1,8-diazabicyclo[5,4,0]-7-undecene [DBU] (22.6 g) and triphenylmethyl chloride [TPC] (16.2 g) were mixed and water (0.4 ml) was added, and the reaction mixture was stirred at 30.5° C. for 1 hour and then at 48 to 52° C. for 2 hours. The reaction mixture was cooled to 15° C. and water (0.6 ml) was added, and 4-chloromethyl-5-methyl-1,3-dioxol-2-one [DMDO-Cl] (14.67 g) was poured in and the reaction mixture was stirred at 28 to 30° C. for 3 hours and then at 48 to 52° C. for 3.5 hours.

(2) Obtaining Crude Crystals of Trityl Olmesartan Medoxomil

The reaction mixture was cooled to 28 to 32° C. and water (64 ml) was poured in, and the reaction mixture was stirred at 15 to 25° C. for 30 minutes, cooled to 0 to 5° C. and stirred for 30 minutes. The precipitated crystals were filtered out and washed with acetone-water (98 ml), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (47.45 g) were obtained.

(3) Obtaining Purified Crystals of Trityl Olmesartan Medoxomil

Acetone (174.6 ml), wet crude crystals of trityl olmesartan medoxomil (42.75 g) and active carbon (0.77 g) were mixed, and the reaction mixture was stirred at 50° C. for 45 minutes. The active carbon was filtered out of the reaction mixture and washed with acetone (17.4 ml). After water (58 ml) was poured into the filtrate at 30° C., it was stirred at 28 to 32° C. for 30 minutes, and water (6.7 ml) was further poured in and the reaction mixture was cooled to 0 to 5° C. The precipitated crystals were filtered out and washed with acetone-water (88 ml) and water (88 ml), and a wet product of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [purified crystals of trityl olmesartan medoxomil] (38.56 g) was obtained.

(4) Wet purified crystals of trityl olmesartan medoxomil (34.71 g) were subjected to a detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of high-purity olmesartan medoxomil] (18.23 g).

Example 2

(1) Tritylation and DMDO Esterification Reactions

To a mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (20 g), acetone (155 ml), 1,8-diazabicyclo[5,4,0]-7-undecene [DBU] (18.4 g) and triphenylmethyl chloride [TPC] (16.28 g), water (0.4 ml) was added, and the reaction mixture was stirred at 31.8° C. for 1 hour and then at 48 to 52° C. for 2 hours. The reaction mixture was cooled to 15° C. and water (0.6 ml) and 4-chloromethyl-5-methyl-1,3-dioxol-2-one [DMDO-Cl] (12.12 g) were added, and the reaction mixture was stirred at 28 to 30° C. for 3 hours and then at 48 to 52° C. for 3.5 hours.

(2) Crude Crystals of Trityl Olmesartan Medoxomil

The reaction mixture was cooled to 28 to 32° C. and water (64 ml) was poured in, and the reaction mixture was stirred at 15 to 25° C. for 30 minutes and then cooled to 0 to 5° C. The precipitated crystals were filtered out and washed with acetone-water (98 ml), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5- yl]biphenyl-4-yl]methyl]imidazole-5-carboxylate [crude crystals of trityl olmesartan medoxomil] (49.36 g) were obtained.

(3) Purified Crystals of Trityl Olmesartan Medoxomil

A mixture of acetone (174.6 ml), wet crude crystals of trityl olmesartan medoxomil (44.46 g) and active carbon (0.77 g) was stirred at 48 to 52° C. for 50 minutes. The active carbon was filtered out and washed with acetone (17.4 ml). After water (58 ml) was poured into the filtrate at 30° C., it was stirred at 28 to 32° C. for 30 minutes, and water (6.7 ml) was further poured in and the reaction mixture was cooled to 0 to 5° C. The precipitated crystals were filtered out and washed with acetone-water (88 ml) and water (88 ml), and a wet product of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [purified crystals of trityl olmesartan medoxomil] (38.17 g) was obtained.

(4) Wet purified crystals of trityl olmesartan medoxomil (34.37 g) were subjected to a detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of high-purity olmesartan medoxomil] (18.18 g).

Example 3

(1) Tritylation and DMDO Esterification Reactions

To a mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (20.33 g), acetone (160 ml), 1,8-diazabicyclo[5,4,0]-7-undecene [DBU] (18.41 g) and triphenylmethyl chloride [TPC] (16.56 g), water (0.4 ml) was added, and the reaction mixture was stirred at 48 to 52° C. for 2.5 hours. The reaction mixture was cooled to 15 to 20° C. and water (0.6 ml) and 4-chloromethyl-5-methyl-1,3-dioxol-2-one [DMDO-Cl] (12.2 g) were poured in, and the reaction mixture was stirred at 28 to 30° C. for 3 hours and then at 48 to 52° C. for 3 hours.

(2) Crude Crystals of Trityl Olmesartan Medoxomil

The reaction mixture was cooled to 28 to 32° C. and water (66 ml) was poured in, and the reaction mixture was stirred at 15 to 25° C. for 30 minutes, cooled to 0 to 5° C. and stirred for 30 minutes. The precipitated crystals were filtered out and washed with acetone-water (100 ml), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (44.8 g) were obtained.

(3) Purified Crystals of Trityl Olmesartan Medoxomil

A mixture of acetone (180 ml), wet crude crystals of trityl olmesartan medoxomil (40.32 g) and active carbon (1.58 g) was stirred at 45 to 55° C. for 36 minutes. The active carbon was filtered out and washed with acetone (18 ml). After water (60 ml) was poured into the filtrate at 23.4° C., it was stirred at 15 to 35° C. for 30 minutes, and water (6.8 ml) was further poured in and the reaction mixture was cooled to 0 to 5° C. The crystals were filtered out and washed with acetone-water (90 ml) and water (90 ml), and then dried under reduced pressure while the temperature was raised to 40° C. (5-Methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [purified crystals of trityl olmesartan medoxomil] (30.04 g) was obtained.

(4) Purified crystals of trityl olmesartan medoxomil (27.04 g) were subjected to a detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of high-purity olmesartan medoxomil] (18.29 g).

Example 4

(1) Tritylation and DMDO Esterification Reactions

To a mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (10.53 g), acetone (80 ml), 1,8-diazabicyclo[5,4,0]-7-undecene [DBU] (11.6 g) and triphenylmethyl chloride [TPC] (8.22 g), water (0.185 ml) was added, and the reaction mixture was stirred at 30 to 35° C. for 35 minutes and then at 48 to 52° C. for 2.5 hours. The reaction mixture was cooled to 15° C. and 4-chloromethyl-5-methyl-1,3-dioxol-2-one [DMDO-Cl] (7.45 g) was poured in, and the reaction mixture was stirred at 30° C. for 2.5 hours and then at 50° C. for 3 hours.

(2) Crude Crystals of Trityl Olmesartan Medoxomil

The reaction mixture was cooled to 28 to 32° C. and water (33 ml) was poured into the reaction mixture, and the reaction mixture was stirred at 20° C. for 30 minutes, cooled to 0 to 5° C. and stirred for 30 minutes. The precipitated crystals were filtered out and washed with acetone-water (50 ml) and then dried in vacuo to obtain crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (17.79 g).

Example 5

(1) Tritylation and DMDO Esterification Reactions

To a mixture of acetone (1633.4 L), 4-(1-hydroxy-1-methylethyl)-2-propyl-1-[[2'-[1H-tetrazol-5-yl]biphenyl-4-yl]methyl]imidazole-5-carboxylic acid [olmesartan] (210 kg), 1,8-diazabicyclo[5,4,0]-7-undecene [DBU] (237 kg) and triphenylmethyl chloride [TPC] (168 kg), water (4.2 kg) was added, and the reaction mixture was stirred at 48 to 54° C. for 2 hours. The reaction mixture was cooled to 10 to 20° C. and water (6 kg) and 4-chloromethyl-5-methyl-1,3-dioxol-2-one [DMDO-Cl] (154 kg) were poured in, and the reaction mixture was stirred at 28 to 32° C. for 3 hours and then at 48 to 52° C. for 3.5 hours.

(2) Crude Crystals of Trityl Olmesartan Medoxomil

The reaction mixture was cooled to 28 to 32° C. and water (672 L) was poured in, and the reaction mixture was stirred at 15 to 25° C. for 30 minutes, cooled to 0 to 5° C. and stirred for 30 minutes. The crystals were subjected to centrifugal filtration and washed with acetone-water (765 L), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] were obtained.

(3) Purified Crystals of Trityl Olmesartan Medoxomil

A mixture of acetone (2039.9 L), wet crude crystals of trityl olmesartan medoxomil (whole amount) and active carbon (7.2 kg) was stirred at 45 to 55° C. for 1 hour. The active carbon was filtered out and washed with acetone (204.7 L). After water (678 L) was poured into the filtrate at 25 to 35° C., water (78 L) was poured in at 25.4° C., and the reaction mixture was cooled to 0 to 5° C. The crystals were subjected to centrifugal filtration and washed with acetone-water (873

L) and further water (873 L), and a wet product of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [purified crystals of trityl olmesartan medoxomil] (405.2 kg) was obtained.

(4) Wet purified crystals of trityl olmesartan medoxomil (405.2 kg) were subjected to a detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of high-purity olmesartan medoxomil] (227.81 kg).

Example 6

(1) Tritylation and DMDO Esterification Reactions

To a mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (10.53 g), acetone (80 ml), 1,8-diazabicyclo[5,4,0]-7-undecene [DBU] (11.6 g) and triphenylmethyl chloride [TPC] (8.22 g), water (0.185 ml) was added, and the reaction mixture was stirred at 30 to 35° C. for 1 hour and then at 50° C. for 3 hours. The reaction mixture was cooled to 15° C. and water (0.615 ml) and 4-chloromethyl-5-methyl-1,3-dioxol-2-one [DMDO-Cl] (7.45 g) were poured in, and the reaction mixture was stirred at 30° C. for 2.5 hours and then at 50° C. for 4.5 hours.

(2) Crude Crystals of Trityl Olmesartan Medoxomil

The reaction mixture was cooled to 28° C. and water (33 ml) was poured into the reaction mixture, and the reaction mixture was stirred at 20° C. for 40 minutes, cooled to 0 to 5° C. and stirred for 30 minutes. The obtained product was filtered and dried in vacuo, and crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (18.09 g) were obtained.

Example 7

(1) Tritylation and DMDO Esterification Reactions

To a mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (10.53 g), acetone (80 ml), 1,8-diazabicyclo[5,4,0]-7-undecene [DBU] (11.6 g) and triphenylmethyl chloride [TPC] (8.22 g), water (0.185 ml) was added, and the reaction mixture was stirred at 30 to 35° C. for 1 hour and then at 48 to 52° C. for 3 hours. The reaction mixture was cooled to 15 to 20° C. and water (0.95 ml) and 4-chloromethyl-5-methyl-1,3-dioxol-2-one [DMDO-Cl] (7.45 g) were poured in, and the reaction mixture was stirred at 30° C. for 2.5 hours and then at 50° C. for 4.5 hours.

(2) Crude Crystals of Trityl Olmesartan Medoxomil

The reaction mixture was cooled to 28 to 32° C. and water (33 ml) was poured into the reaction mixture, and the reaction mixture was stirred at 20° C. for 30 minutes, cooled to 0 to 5° C. and stirred for 30 minutes. The obtained product was filtered, washed with acetone-water (50 ml) and dried in vacuo, and crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (17.54 g) were obtained.

Reference Example 1

(1) Tritylation and DMDO Esterification Reactions

A mixture of 4-(1-hydroxy-1-methylethyl)-2-propyl-1-[[2'-[1H-tetrazol-5-yl]biphenyl-4-yl]methyl]imidazole-5-carboxylic acid [olmesartan] (35.6 g), acetone (280 ml), 1,8-diazabicyclo[5,4,0]-7-undecene [DBU] (40.56 g) and triphenylmethyl chloride [TPC] (28.8 g) was reacted at 48 to 52° C. for 2 hours. 4-Chloromethyl-5-methyl-1,3-dioxol-2-one [DMDO-Cl] (26.1 g) was poured into the reaction mixture and it was reacted at 30° C. for 3 hours and then at 50° C. for 3 hours.

(2) Crude Crystals of Trityl Olmesartan Medoxomil

The reaction mixture was cooled to 28 to 32° C. and water (116 ml) was poured in, and the reaction mixture was stirred at 15 to 35° C. for 30 minutes, cooled to 0 to 5° C. and stirred for 30 minutes. The precipitated crystals were filtered out and washed with acetone-water (175 ml), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crude crystals of trityl olmesartan medoxomil] (74.14 g) were obtained.

(3) Crystals of Trityl Olmesartan Medoxomil

A mixture of acetone (350 ml), wet crude crystals of trityl olmesartan medoxomil (73.16 g) and active carbon (3 g) was stirred at 45 to 55° C. for 30 minutes. The active carbon was filtered out and washed with acetone (35 ml). After water (130 ml) was poured into the filtrate at 28.5° C., it was stirred at 15 to 35° C. for 30 minutes and then cooled to 0 to 5° C. and stirred for 30 minutes. The crystals were filtered out and washed with acetone-water (175 ml) and water (175 ml), and a wet product of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crystals of trityl olmesartan medoxomil] (82.15 g) was obtained.

(4) Crystals of trityl olmesartan medoxomil (80.15 g) were subjected to a detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of olmesartan medoxomil] (36.70 g).

Reference Example 2

(1) Tritylation and DMDO Esterification Reactions

A mixture of acetone (440.5 L), 4-(1-hydroxy-1-methylethyl)-2-propyl-1-[[2'-[1H-tetrazol-5-yl]biphenyl-4-yl]methyl]imidazole-5-carboxylic acid [olmesartan] (58.2 kg), 1,8-diazabicyclo[5,4,0]-7-undecene [DBU] (63.8 kg) and triphenylmethyl chloride [TPC] (44.9 kg) was reacted at 48 to 52° C. for 2.5 hours. The reaction mixture was cooled to 25.1° C. and 4-chloromethyl-5-methyl-1,3-dioxol-2-one [DMDO-Cl] (41.1 kg) was poured in, and the reaction mixture was reacted at 28 to 32° C. for 3 hours and then at 48 to 52° C. for 3 hours.

(2) Crude Crystals of Trityl Olmesartan Medoxomil

The reaction mixture was cooled to 28 to 32° C. and water (182 L) was poured into the reaction mixture, and it was stirred at 15 to 25° C. for 30 minutes, cooled to 0 to 5° C. and stirred for 30 minutes. The crystals were subjected to centrifugal filtration and washed with acetone-water (276.1 L), and wet crude crystals of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]

imidazole-5-carboxylate [crude crystals of trityl olmesartan medoxomil] (110.3 kg) were obtained.

(3) Crystals of Trityl Olmesartan Medoxomil

A mixture of acetone (550.5 L), wet crude crystals of trityl olmesartan medoxomil (110.3 kg) and active carbon (4.7 kg) was stirred at 45 to 55° C. for 40 minutes. The active carbon was filtered out and washed with acetone (83.5 L). After water (216 L) was poured into the filtrate at 15 to 35° C., it was stirred for 15 minutes and cooled to 0 to 5° C. The crystals were subjected to centrifugal filtration and washed with acetone-water (276.1 L) and water (275 L), and a wet product of (5-methyl-2-oxo-1,3-dioxolen-4-yl)methyl 4-(1-hydroxy-1-methylethyl)-2-propyl-1-[[2'-[2-(triphenylmethyl)-2H-tetrazol-5-yl]biphenyl-4-yl]methyl]imidazole-5-carboxylate [crystals of trityl olmesartan medoxomil] (107.77 kg) was obtained.

(4) Wet crystals of trityl olmesartan medoxomil (107.72 kg) were subjected to detritylation reaction to obtain (5-methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [crystals of olmesartan medoxomil] (61.57 kg).

(Production of Impurity Sample)

(Olmesartan Medoxomil Dehydrate (Compound B))

(5-Methyl-2-oxo-1,3-dioxolen-4-yl)methyl 4-(1-hydroxy-1-methylethyl)-2-propyl-1-[[2'-(1H-tetrazol-5-yl)biphenyl-4-yl]methyl]imidazole-5-carboxylate [olmesartan medoxomil] (20.0 g) was added into anhydrous N,N-dimethylacetamide (80 ml) under a nitrogen stream, and after dissolution was confirmed, concentrated sulfuric acid (3.0 ml) was poured in and the mixture was reacted at about 100° C. for 2.5 hours. Upon completion of the reaction, the reaction mixture was cooled to about 40° C. and poured into cold water (80 ml). After methylene chloride (80 ml) was poured in, the pH of the reaction mixture was adjusted to 4.2 with 25% sodium hydroxide. The organic layer was separated, washed with brine (80 ml) and concentrated under reduced pressure to obtain 22.58 g of (5-methyl-2-oxo-1,3-dioxolen-4-yl)methyl 4-isopropenyl-2-propyl-1-[[2'-[1H-tetrazol-5-yl]biphenyl-4-yl]methyl]imidazole-5-carboxylate [crude olmesartan medoxomil dehydrate] as a foam.

The obtained crude olmesartan medoxomil dehydrate was dissolved in methylene chloride (45 ml) and adsorbed onto silica gel (340 g), and separated by silica gel chromatography using a solvent system of methylene chloride and ethanol with a mixing ratio of 99:1 to 99:5, and the eluent was concentrated under reduced pressure to obtain 7.84 g of high-quality olmesartan medoxomil dehydrate (Compound B).

Mass spectrum (FAB) m/z: 541 (M+H)$^-$ $^1$H-NMR spectrum (DMSO-$d_6$): δ ppm 0.87(3H, t, J=7.3 Hz), 1.53-1.63(2H, m), 2.02(3H, s), 2.11(3H, s), 2.58(2H, t, J=7.6 Hz), 5.03(2H, s), 5.18(1H, s), 5.24(1H, s), 5.45(2H, s), 6.92(2H, d, J=8.1 Hz), 7.05(2H, d, J=8.1 Hz), 7.52-7.68(4H, m)

(Trityl Olmesartan Medoxomil Dehydrate (Tritylated Compound B))

4-Isopropenyl-2-propyl-1-[[2'-(1H-tetrazol-5-yl)biphenyl-4-yl]methyl]imidazole-5-carboxylic acid [olmesartan dehydrate, compound 34b described in J. Med. Chem., 39, 323-338 (1996)] (139.36 g), acetone (1022.3 ml), 1,8-diazabicyclo[5,4,0]-7-undecene [DBU] (154.3 g) and triphenylmethyl chloride [TPC] (109.6 g) were mixed and the mixture was stirred at 48 to 52° C. for 5 hours. The reaction mixture was cooled to 20° C. and 4-chloromethyl-5-methyl-1,3-dioxol-2-one [DMDO-Cl] (99.1 g) was added, and the reaction mixture was stirred at 48 to 52° C. for 2.5 hours and then at 55 to 58° C. for 1.5 hours. 1,8-Diazabicyclo[5,4,0]-7-undecene [DBU] (45.4 g) and 4-chloromethyl-5-methyl-1,3-dioxol-2-one [DMDO-Cl] (49.5 g) were added to the reaction mixture and the reaction mixture was stirred at 56 to 57° C. for 5 hours. The reaction mixture was concentrated under reduced pressure and the residue was dissolved in ethyl acetate (3000 ml) and water (1000 ml) and extracted 4 times. The obtained organic layer was concentrated under reduced pressure to obtain 327.83 g of (5-methyl-2-oxo-1,3-dioxolen-4-yl)methyl 4-isopropenyl-2-propyl-1-[[2'-[2-(triphenylmethyl)-2H-tetrazol-5-yl]biphenyl-4-yl] methyl]imidazole-5-carboxylate [crude trityl olmesartan medoxomil dehydrate] as an oil.

The obtained crude trityl olmesartan medoxomil dehydrate was dissolved in ethyl acetate (500 ml) and adsorbed onto silica gel (1700 g), and separated by silica gel chromatography using a solvent system of n-hexane and ethyl acetate with a mixing ratio of 8:2 to 3:7, and the eluent was concentrated under reduced pressure to obtain 68.8 g of high-quality trityl olmesartan medoxomil dehydrate (tritylated Compound B).

$^1$H-NMR spectrum (CDCl$_3$): δ ppm 0.89(3H, t, J=7.4 Hz), 1.60-1.74(2H, m), 2.03(3H, s), 2.12(3H, s), 2.54(2H, t, J=7.8 Hz), 4.76(2H, 2), 5.26(1H, s), 5.29(1H, s), 5.37(2H, s), 6.75 (2H, d, J=8.1 Hz), 6.94-6.97(6H, m), 7.08(2H, d, J=8.1 Hz), 7.24-7.52(12H, m), 7.87(1H, dd, J=7.9, 1.3 Hz)

Mass spectrum (FAB) m/z: 783 (M+H)$^-$ (Method of Measuring Contents of Olmesartan Medoxomil and Impurity)

Measuring Conditions (Liquid Chromatography Method)

Detector: Ultraviolet absorptiometer (measuring wavelength: 250 nm)

Analysis column: Stainless steel tube with an inner diameter of 4.6 mm and a length of 10 cm was packed with 3.5 μm of octylsilylated silica gel for liquid chromatography.

Guard column: Stainless steel tube with an inner diameter of 4.6 mm and a length of 5 cm was packed with filler for liquid chromatography (and installed immediately after a liquid delivery pump at the mobile phase A end of a high-pressure gradient system).

Column temperature: Constant temperature near 40° C.

Mobile phase A: A mixture of 0.015 mol/L phosphate buffer (pH 3.5)/acetonitrile (4:1)

Mobile phase B: A mixture of acetonitrile/0.015 mol/L phosphate buffer (pH 3.5) (4:1)

Flow rate: Adjusted so that retention time of olmesartan medoxomil is approximately 10 minutes (constant rate of approximately 1 ml/min).

Mobile phase delivery: The mixing ratio of mobile phase A and mobile phase B is changed to control the concentration gradient as follows.

TABLE 1

| Time from pouring of sample (min) | Mobile phase A (%) | Mobile phase B (%) |
| --- | --- | --- |
| 0-10 | 75 | 25 |
| 10-35 | 75 >> 0 (linear gradient) | 25 >> 100 (linear gradient) |
| 35-45 | 0 | 100 |

(Method of Measuring Contents of Trityl Olmesartan Medoxomil and Impurity)

Measuring Conditions (Liquid Chromatography Method)

Detector: Ultraviolet absorptiometer (measuring wavelength: 225 nm)

Analysis column: Stainless steel tube with an inner diameter of 4.6 mm and a length of 25 cm was packed with 5 μm of octylsilylated silica gel for liquid chromatography.

Column temperature: Constant temperature near 40° C.

Mobile phase A: 0.005 mol/L phosphoric acid solution
Mobile phase B: Acetonitrile
Flow rate: Adjusted so that retention time of trityl olmesartan medoxomil is approximately 10 minutes (constant rate of approximately 1 ml/min).
Mobile phase delivery: The mixing ratio of mobile phase A and mobile phase B is changed to control the concentration gradient as follows.

TABLE 2

| Time from pouring of sample (min) | Mobile phase A (%) | Mobile phase B (%) |
|---|---|---|
| 0-20 | 30 | 70 |
| 20-25 | 30 >> 10 (linear gradient) | 70 >> 90 (linear gradient) |
| 25-45 | 10 | 90 |

TABLE 3

(Measured values of contents of olmesartan medoxomil and impurity)

| | Water content | | OLM Purity | | |
|---|---|---|---|---|---|
| | Water in the reaction mixture (w/w) % | Added water (w/w) % | OLM content % | Compound A % | Compound B % |
| Example 1 | 0.70 | 5.0 | 99.58 | 0.14 | 0.15 |
| | | | 99.58 *1 | 0.06 *2 | 0.17 *3 |
| Example 2 | 0.71 | 5.0 | 99.58 | 0.15 | 0.19 |
| | | | 99.62 *1 | 0.07 *2 | 0.13 *3 |
| Example 3 | 0.75 | 4.9 | 99.61 | 0.07 | 0.21 |
| | | | 99.45 *1 | 0.12 *2 | 0.19 *3 |
| Example 4 | 0.35 | 1.8 | — *5 | — *5 | — *5 |
| | | | 99.36 *1 | 0.15 *2 | 0.23 *3 |
| Example 5 | 0.70 | 4.9 | 99.66 | 0.07 | 0.15 |
| | | | 99.6 *1 | ND *2*4 | 0.1 *3 |
| Example 6 | 1.00 | 7.6 | — *5 | — *5 | — *5 |
| | | | 99.33 *1 | 0.15 *2 | 0.15 *3 |
| Example 7 | 1.35 | 10.8 | — *5 | — *5 | — *5 |
| | | | 99.23 *1 | 0.26 *2 | 0.13 *3 |
| Reference Example 1 | 0.22 | 0 | 99.34 | 0.13 | 0.43 |
| | | | 99.50 *1 | 0.09 *2 | 0.38 *3 |
| Reference Example 2 | 0.25 | 0 | 99.14 | 0.04 | 0.32 |
| | | | 99.51 *1 | 0.03 *2 | 0.33 *3 |

The OLM content and impurity content are indicated as area percentages (%) measured by liquid chromatography method described above.

In the table, "water in the reaction mixture" indicates the ratio (w/w) % of the total water content to the reaction mixture during the tritylation and DMDO esterification reactions. "Added water" indicates the ratio (w/w) % of added water to olmesartan as a starting material in the tritylation and DMDO esterification reactions.

OLM represents olmesartan medoxomil, Compound A represents olmesartan and Compound B represents olmesartan medoxomil dehydrate.

1 denotes the purity of trityl olmesartan medoxomil in crystals of trityl olmesartan medoxomil obtained in the tritylation and DMDO esterification reactions.
2 denotes the content of trityl olmesartan in crystals of trityl olmesartan medoxomil obtained in the tritylation and DMDO esterification reactions.
3 denotes the content of trityl olmesartan medoxomil dehydrate in crystals of trityl olmesartan medoxomil obtained in the tritylation and DMDO esterification reactions.
4 denotes "undetected" (below the detection limit).
5 denotes "unmeasured".

In Example 1, Example 2, Example 3, Example 5, Reference Example 1 and Reference Example 2, olmesartan was subjected to tritylation and DMDO esterification reactions, and then to a detritylation step to obtain olmesartan medoxomil. The impurity content was evaluated by analyzing the purity and the impurity content of olmesartan medoxomil as the final product.

In Example 4, Example 6 and Example 7, reactions up to the tritylation and DMDO esterification reactions of olmesartan were carried out. In these examples, the purity and the impurity content of trityl olmesartan medoxomil, as a synthetic intermediate of olmesartan medoxomil, were analyzed to estimate the purity and the impurity content of olmesartan medoxomil which is obtained by converting to the final product. Trityl olmesartan medoxomil, trityl olmesartan and trityl olmesartan medoxomil dehydrate as synthetic intermediates correspond to olmesartan medoxomil, olmesartan and olmesartan medoxomil dehydrate as final products, respectively. A trityl group is removed in the detritylation reaction, and the content of olmesartan medoxomil dehydrate is preserved in the detritylation reaction.

In Examples 1 to 7, in which water was added to the reaction mixture in the tritylation step and the DMDO esterification step, the amount of olmesartan medoxomil dehydrate (Compound B) produced was clearly reduced in comparison to Reference Examples 1 and 2 in which no water was added. Despite concerns that the addition of water would increase the production of olmesartan (Compound A) which is formed by hydrolysis of the DMDO ester, a significant increase was not observed with optimal water content.

Industrial Applicability

In the present invention, high-purity olmesartan medoxomil in which the contents of impurities such as olmesartan and olmesartan medoxomil dehydrate, especially the content of olmesartan medoxomil dehydrate, are reduced and a method for producing it, are provided.

The invention claimed is:

1. A method for producing olmesartan medoxomil comprising
   (a) producing trityl olmesartan medoxomil by
      (i) reacting olmesartan with trityl halide and then
      (ii) reacting it with DMDO halide,
   in a solvent in the presence of a base, wherein water is present in the reaction mixture in the tritylation step (i) and the DMDO esterification step (ii); and
   (b) removing the trityl group from trityl olmesartan medoxomil.

2. The production method according to claim 1, wherein the water content in the reaction mixture is 0.3 (w/w) % or more.

3. The production method according to claim 1, wherein the water content in the reaction mixture is from 0.3 to 3.0 (w/w) %.

4. The production method according to claim 1, wherein the water content in the reaction mixture is from 0.3 to 1.5 (w/w) %.

5. The production method according to claim 1, wherein the water content in the reaction mixture is from 0.4 to 1.3 (w/w) %.

6. The production method according to claim 1, wherein 1.0 to 28 (w/w) % water to olmesartan is added to the reaction mixture.

7. The production method according to claim 1, wherein 1.0 to 13 (w/w) % water to olmesartan is added to the reaction mixture.

8. The production method according to claim 1, wherein 2.0 to 10 (w/w) % water to olmesartan is added to the reaction mixture.

9. The production method according to claim 1, wherein the reaction solvent is used in a 5 to 20 (v/w)-fold amount to olmesartan.

10. The production method according to claim1, wherein the reaction solvent is acetone.

11. The production method according to claim 1, wherein the base is 1,8-diazabicyclo[5,4,0]-7-undecene.

12. The production method according to claim 1, wherein the halide portion of the trityl halide and the DMDO halide is chloride.

13. The production method according to claim 1, wherein the olmesartan medoxomil comprises 0.3% or less of olmesartan medoxomil dehydrate.

14. The production method according to claim 1, wherein the olmesartan medoxomil comprises 0.25% or less of olmesartan medoxomil dehydrate.

15. The production method according to claim 1, wherein the olmesartan medoxomil comprises 0.2% or less of olmesartan medoxomil dehydrate.

16. The production method according to claim 1, wherein the olmesartan medoxomil comprises 0.15% or less of olmesartan.

* * * * *